United States Patent
Marashdeh et al.

(10) Patent No.: US 10,502,655 B2
(45) Date of Patent: Dec. 10, 2019

(54) MAGNETIC PRESSURE SENSORS SYSTEM FOR MEASUREMENT AND IMAGING OF STEEL MASS

(71) Applicant: Tech4Imaging LLC, Columbus, OH (US)

(72) Inventors: Qussai Marashdeh, Columbus, OH (US); Mohd Harish, Columbus, OH (US); Christopher Zuccarelli, Columbus, OH (US)

(73) Assignee: Tech4Imaging LLC, Columbus, OH (US)

( * ) Notice: Subject to any disclaimer, the term of this patent is extended or adjusted under 35 U.S.C. 154(b) by 149 days.

(21) Appl. No.: 15/452,023

(22) Filed: Mar. 7, 2017

(65) Prior Publication Data
US 2018/0259487 A1    Sep. 13, 2018

(51) Int. Cl.
*G01M 5/00*    (2006.01)
*G01N 17/00*    (2006.01)

(52) U.S. Cl.
CPC ........ *G01M 5/0091* (2013.01); *G01M 5/0033* (2013.01); *G01M 5/0075* (2013.01); *G01M 5/0083* (2013.01); *G01N 17/006* (2013.01)

(58) Field of Classification Search
CPC . G01N 27/904; G01N 17/006; G01N 27/9046
See application file for complete search history.

(56) References Cited

U.S. PATENT DOCUMENTS

| | | | |
|---|---|---|---|
| 4,908,578 A | 3/1990 | Van Liere | |
| 5,130,661 A | 7/1992 | Beck et al. | |
| 5,262,730 A | 11/1993 | Smith et al. | |
| 5,279,163 A * | 1/1994 | D'Antonio | A61B 5/087 336/30 |
| 5,818,222 A | 10/1998 | Ramsden | |
| 6,208,204 B1 | 3/2001 | Suzuki et al. | |
| 7,424,462 B2 | 9/2008 | Avni et al. | |
| 7,684,846 B2 | 3/2010 | Johnson et al. | |
| 8,461,852 B2 | 6/2013 | Yang et al. | |
| 8,508,238 B2 | 8/2013 | Mahalingam et al. | |

(Continued)

FOREIGN PATENT DOCUMENTS

| | | |
|---|---|---|
| CN | 102954854 A | 3/2013 |
| EP | 0606115 A1 | 7/1994 |

(Continued)

OTHER PUBLICATIONS

Marashdeh, et al., "On the ECT Sensor Based Dual Imaging Modality System for Electrical Permittivity and Conductivity Measurements", 2006, pp. 1-6, The Ohio State University, Columbus, Ohio.

(Continued)

*Primary Examiner* — Akm Zakaria
(74) *Attorney, Agent, or Firm* — Standley Law Group LLP

(57) ABSTRACT

The present invention uses a magnetic source and pressure sensors mounted against a surface. Based on the mass of metal inside a volume, the magnetic source is attracted to the surface and exerts pressure on the pressure sensor that is proportional to the mass of metal being detected. An electronic device reads the pressure value and uses the information to quantify the metal in the surface or inside the volume of the construction component.

17 Claims, 8 Drawing Sheets

Extended 4MaPS system for external tendon

(56) References Cited

U.S. PATENT DOCUMENTS

| | | |
|---|---|---|
| 8,519,722 B1 | 8/2013 | Prendergast |
| 8,614,707 B2 | 12/2013 | Warsito et al. |
| 8,867,928 B2 | 10/2014 | Piehler |
| 9,016,143 B2 | 4/2015 | Mamigonians |
| 9,170,224 B2 | 10/2015 | Fan et al. |
| 9,259,168 B2 | 2/2016 | Marashdeh et al. |
| 9,579,038 B2 | 2/2017 | Brunner et al. |
| 9,581,560 B2 | 2/2017 | Fan et al. |
| 2002/0028010 A1 | 3/2002 | Toida |
| 2003/0020493 A1 | 1/2003 | Haase et al. |
| 2003/0173958 A1* | 9/2003 | Goldfine ............ G01L 5/0047 324/209 |
| 2004/0233191 A1 | 11/2004 | Mukherjee et al. |
| 2005/0167588 A1 | 8/2005 | Donnangelo |
| 2007/0024278 A1* | 2/2007 | Walters ............ G01N 27/902 324/242 |
| 2007/0133746 A1 | 6/2007 | Ortiz Aleman et al. |
| 2008/0116995 A1 | 5/2008 | Kim et al. |
| 2009/0271146 A1 | 10/2009 | Ammar |
| 2009/0272028 A1* | 11/2009 | Drozd ............ C10L 5/14 44/569 |
| 2010/0132473 A1 | 6/2010 | Willcox |
| 2010/0148804 A1 | 6/2010 | Jakoby et al. |
| 2010/0332170 A1 | 12/2010 | Gao et al. |
| 2011/0109911 A1 | 5/2011 | Podoleanu |
| 2012/0242350 A1 | 9/2012 | Sundaresan et al. |
| 2012/0268135 A1* | 10/2012 | Marsala ............ G01V 3/30 324/338 |
| 2013/0187641 A1* | 7/2013 | Singer ............ G01N 27/82 324/220 |
| 2013/0275082 A1 | 10/2013 | Follmer et al. |
| 2013/0327154 A1 | 12/2013 | Xie et al. |
| 2014/0361793 A1 | 12/2014 | Marashdeh et al. |
| 2014/0365009 A1* | 12/2014 | Wettels ............ B25J 9/1612 700/258 |
| 2014/0365152 A1 | 12/2014 | Marashdeh et al. |
| 2015/0048852 A1 | 2/2015 | Marshdeh et al. |
| 2015/0338364 A1 | 11/2015 | Fan et al. |
| 2016/0025663 A1 | 1/2016 | Lehikoinen et al. |
| 2016/0076926 A1 | 3/2016 | McCann et al. |
| 2016/0091448 A1 | 3/2016 | Soleimani |
| 2016/0111192 A1 | 4/2016 | Suzara |
| 2016/0206227 A1 | 7/2016 | Marashdeh et al. |
| 2016/0310040 A1 | 10/2016 | Marashdeh |
| 2016/0327503 A1 | 11/2016 | Marashdeh et al. |

FOREIGN PATENT DOCUMENTS

| | | |
|---|---|---|
| WO | 2010007096 A1 | 1/2010 |
| WO | 2011002793 A1 | 1/2011 |

OTHER PUBLICATIONS

Warsito, et al., "Electrical Capacitance Volume Tomography", 2007, pp. 1-9.

Covilakam, M., "Evaluation of Structural Monitoring Methods for Large Diameter Water Transmission Pipelines", Dec. 2011, The University of Texas at Arlington.

Chew, W. et al., Reconstruction of Two-Dimensional Permittivity Distribution Using the Distorted Born Iterative Method, IEEE Transactions on Medical Imaging, Jun. 1990, pp. 218-225, vol. 9, No. 2.

Marashdeh, Q. et al., Adaptive Electrical Capacitance Volume Tomography, IEEE Sensors Journal, Apr. 2014, pp. 1253-1259, vol. 14, No. 4.

Xie, C. et al., Electrical Capacitance Tomography for Flow Imaging: System Model for Development of Image Reconstruction Algorithms and Design of Primary Sensors, IEEE Proceedings-G, Feb. 1992, pp. 89-98, vol. 139, No. 1.

Yang, W. et al., Image Reconstruction Algorithms for Electrical Capacitance Tomography, Measurement Science and Technology 14, 2003, pp. R1-R13.

Huang et al., Design of Sensor Electronics for Electrical Capacitance Tomography, IEE Proceedings G (Circuits, Devices and Systems), vol. 139, Issue 1, Feb. 1992, p. 83-88.

Gunes, C. et al., A Comparison Between Electrical Capacitance Tomography and Displacement—Current Phase Tomography, IEEE Sensors Journal, Dec. 15, 2017, vol. 17, No. 24.

Wang, F. et al., Electrical Capacitance Volume Tomography: Design and Applications, Sensors, 2010 pp. 1890-1917.

Wikipedia, Electrical Capacitance Volume Tomography, https://en.wikipedia.org/w/index.php?title=Electrical_capacitance_volume_tomography&oldid=868112998, site visited Dec. 7, 2018.

* cited by examiner

MAGNETIC PRESSURE SENSORS SYSTEM FOR MEASUREMENT AND IMAGING OF STEEL MASS

BACKGROUND OF THE INVENTIVE FIELD

Inspection and measurement of steel mass is critical in many applications. For example, corrosion in pipelines can lead to degradation of pipe strength and possible ruptures. In infrastructure applications, corrosion in steel can lead to reduction in the load-bearing capability that these structures can handle. This can lead to collapse of buildings made with reinforced steel or bridge failures as pre-stressed tendons give away.

Detection of steel mass is especially important in segmental bridges where the bridge's load-bearing ability depends on the steel of pre-stressed tendons. Tendons, in this case, hold the numerous segments of a segmental bridge together. The loading capability of a bridge depends on the number of tendons linking the segments together and the health of steel inside each tendon. A tendon typically fails when steel strands snap; thus increasing the load on other tendons holding the bridge together. If enough tendons snap, the remaining tendons cannot hold the bridge weight together and a bridge collapse is imminent. Another risk factor for tendons is in the form of steel corrosion. Here, the load-bearing capability is weakened when the steel strands inside the tendons corrode. It is critical to continuously inspect these bridge components for corrosion in the tendons and to detect for failed or broken tendons. Corrosion is brought on by air and moisture in contact with steel, as well as by high chloride content within the grouting or fill material surrounding the steel.

Current inspection methods depend on either inaccurate or inefficient methods. For example, magnetic flux is based on generating magnetic field at one side of the tendon and detecting the strength of that field as it is received from a detector end. This method, being the most viable solution that currently exists, has two major drawbacks. First, it is labor and time intensive as it requires repeatedly winding and unwinding heavy cables. Second, it is not very accurate as the magnetic field detected at the receiver end is typically very low. Another method is based on the use of microwave signals transmitted into the structure. A receiver in this case detects the electromagnetic waves as they bounce back from the steel rods. However, this method also suffers from two major drawbacks: First, the steel rods are typically located relatively near to the surface where the sensors are mounted. This makes deciphering the received signals from multiple reflections difficult; and thus accuracy is reduced. Second, this method is more suited to detecting if steel rods are present or not; it cannot accurately detect corrosion of steel mass.

In the present invention, a new system and method is used to overcome the disadvantages in currently existing methods. The new invention uses a magnetic source and pressure sensors mounted against a surface. Based on the mass of steel inside a volume, the magnetic source is attracted to the surface and exerts pressure on the pressure sensor that is proportional to the mass of steel being detected. An electronic device reads the pressure value and uses the information to quantify the steel inside the volume.

A further extension of this invention involves the mounting of several magnetic-pressure sensors around the volume being detected. The collective pressure signals from the sensors are used to map the location of steel inside the volume being tested.

The present invention can be applied wherever there is a need to measure the mass of steel in a non-invasive manner. In addition to infrastructure Non-Destructive Testing (NDT), inspection of pipes for detection of corrosion based on the available thickness of steel is also made possible.

The present invention relates to a system and process to obtain a relationship between pressure exerted on pressure sensors and the area (or volume) of steel in the imaging domain. In one embodiment, multiple sensors are mounted around cylindrical objects like tendons or pipes. In another embodiment, the magnetic-pressure sensor modules are placed on plane or flat surfaces.

Electrical Capacitance Volume Tomography (ECVT) is a non-invasive imaging modality. Its applications span an array of industries. Most notably, ECVT is applicable to multiphase flow applications commonly employed in many industrial processes. ECVT is often the technology of choice due to its advantages of high imaging speed, scalability to different process vessels, flexibility, and safety. In ECVT, sensor plates are distributed around the circumference of the column, object or vessel under interrogation. The number of sensor plates may be increased to acquire more capacitance data. However, increasing the number of sensor plates reduces the area of each sensor plate accordingly. A limit exists on the minimum area of a sensor plate for a given column diameter, thus limiting the maximum number of plates that can be used in an ECVT sensor. This limit is dictated by the minimum signal-to-noise ratio requirement of the data acquisition system. Since ECVT technology is based on recording changes in capacitance measurements induced by changes in dielectric distribution (i.e., phase distribution), and the capacitance level of a particular sensor plate combination is directly proportional to the area of the plates, minimum signal levels are needed to provide sufficiently accurate measurements. These considerations dictate the required minimum sensor plate dimensions. This limitation on the minimum size of the sensor plates, while increasing the number of available sensor plates in an ECVT sensor, is one of the main hurdles in achieving a high resolution imaging system.

To overcome this challenge, the concept of Adaptive Electrical Capacitance Volume Tomography (AECVT) was recently developed, whereby the number of independent capacitance measurements is increased through the use of reconfigurable synthetic sensor plates composed of many smaller sensor plates (constitutive segments). These synthetic sensor plates maintain the minimum area for a given signal-to-noise ratio (SNR) and acquisition speed requirements while allowing for many different combinations of (synthetic) sensor plates in forming a sensor plate pair.

Electrical Capacitance Tomography (ECT) is the reconstruction of material concentrations of dielectric physical properties in the imaging domain by inversion of capacitance data from a capacitance sensor. Electrical Capacitance Volume Tomography or ECVT is the direct 3D reconstruction of volume concentrations or physical properties in the imaging domain utilizing 3D features in the ECVT sensor design. An ECVT system is generally made up of a sensor, sensor electronics and a computer system for reconstruction of the image sensed by the sensor. An ECVT sensor is generally comprised of n electrodes or plates placed around a region of interest, in one embodiment providing $n(n-1)/2$ independent mutual capacitance measurements which are used for image reconstruction. Image reconstruction is performed by collecting capacitance data from the electrodes placed around the wall outside the vessel. ECVT technology is described in U.S. Pat. No. 8,614,707 to Warsito et al. which is hereby incorporated by reference.

Adaptive Electrical Capacitance Volume Tomography (AECVT) provides higher resolution volume imaging of capacitance sensors based on different levels of activation levels on sensor plate segments. In AECVT systems, electrodes are comprised of an array of smaller capacitance segments that may be individually addressed. For example, each segment may be activated with different amplitudes, phase shifts, or frequency to provide the desired sensitivity matrix distribution. The sensor electronics of the present invention is designed to detect and measure the capacitance for the adaptive ECVT sensor of the present invention. For example, the difference in electrical energy stored in the adaptive ECVT sensor would be measured between an empty state and a state where an object is introduced into the imaging domain (e.g., between the electrodes). In a preferred embodiment of the invention, the term "adaptive" means the ability to provide selective or high resolution control through the application of voltage or voltage distributions to a plate having an array of capacitance segments. The change in overall energy of the system due to the introduction of a dielectric material in the imaging domain is used to calculate the change in capacitance related to the dielectric material. The change in capacitance can be calculated from the change in stored energy. Sensor electronics can also be designed by placing individual segment circuits in parallel yielding a summation of currents representing total capacitance between segments under interrogation. By individually addressing the capacitance segments of the electrodes of the present invention, electric field distribution inside the imaging domain can be controlled to provide the desired sensitivity matrix, focus the electric field, and increase overall resolution of reconstructed images. Voltage distribution can also be achieved by using a conventional measuring circuit with a sensor that distributes voltages through a voltage divider.

In AECVT systems, a capacitance measurement circuit is connected to an electrode (detecting or receiving electrode) of the adaptive sensor so that a capacitance measurement can be obtained for the selected source and detecting electrodes. The capacitors Cx1-Cxn of the sensor represent the n number of capacitance segments of the selected source electrode and the detecting electrode. Each capacitance segment of the electrodes can be individually addressed by separated voltage sources. These voltage sources are used for regulating the voltage levels and phase shifts on the capacitance segments of each of the electrodes on the adaptive sensor. The voltage across each of the capacitor segments (Vxn) is the combination of the voltage source Vi and the voltage sources connected to each capacitor segment (Vn). Accordingly, the measured Vo can be used to calculate each of the equivalent capacitance (Cxn) of the capacitance segments of the activated electrode. The associated formula is for Cxn=Cx1=Cx2 . . . =Cxi. For segments with different capacitance values, the equivalent capacitance is calculated using the formula:

$$V_0 = \left(\frac{j\omega R_f}{1 + j\omega C_f R_f}\right)(\Sigma_{i=1}^n V_{xi} C_{xi})$$

As discussed, in one embodiment, n(n−1)/2 independent mutual capacitance measurements are measured and used for image reconstruction. For example, the capacitance between each of the electrodes of the sensor are measured in turn and image reconstruction is performed using this capacitance data. In other words, capacitance measurements are obtained from every pair or electrode combination of the sensor, in turn, to be used in image reconstruction. It is appreciated that the voltage sources herein discussed may be connected to the capacitance segments of each of the electrodes of the sensor array using known switch technologies. Using switches, the system can selectively choose which electrodes to activate by connecting the voltage sources to the selected electrodes through the switches. In another embodiment, switching or multiplexing circuit elements can be used to connect the appropriate voltage sources to each of the capacitance segments of the selected electrode allowing various elements to be selectively connected to each capacitance segment depending on the focus and sensitivity desired. For example, voltage sources of greater amplitude may be switched or connected to the capacitance segments in the center of the electrode or imaging domain so as to focus the measurements towards the center of the electrode or imaging domain.

In an alternate embodiment, instead of using different amplitudes, different frequencies may be used to activate electrode segments enabling concurrent measurements of different capacitance values introduced by electric field beams of different frequencies. In yet another alternate embodiment, different phase shifts may be used to activate electrode segments enabling steering of the electric field inside the imaging domain. The measured change in output voltage can be used to calculate the change in capacitance levels between the capacitance segments which are then used to reconstruct volume images of objects or materials between the sensors. AECVT is described in U.S. Pat. No. 9,259,168 to Marashdeh et al. which is hereby incorporated by reference.

In ECT, ECVT, or AECVT, the capacitance measurement between sensor plates is also related to the effective dielectric content between that plate pair. The SART method can be extended to all measurements of ECT, ECVT, or AECVT sensors, thus providing a high resolution visual representation of each phase through image reconstruction. These previous ECVT systems incorporate data acquisition system that increase imaging resolution through sensing capacitances from 3D conventional and adaptive capacitance sensors. Data acquisition systems are also described in U.S. patent application Ser. No. 14/191,574 (Publication No. US-2014-0365152-A1) which is hereby incorporated by reference.

Electrical capacitance sensors are used for non-invasive imaging by distributing the electric field inside the imaging domain in 3D. ECVT sensors enable sensitivity variation in the imaging domain that can utilize different plate shapes and distributions to target a volume for imaging.

SUMMARY OF THE INVENTION

In one embodiment, the present invention is a system for sensing magnetic pressure in a construction structure of cylindrical shape such as a tube, pipe or tendon, the system comprising: a plurality of pressure sensors adapted to be placed around the construction structure of cylindrical shape; a plurality of magnetic sources, wherein each of the plurality of magnetic sources is paired with one of the plurality of pressure sensors, and wherein the plurality of pressure sensors are adapted to sense pressure from the pressure exerted between the plurality of magnetic sources and the metal in or within the construction structure of cylindrical shape; a processing system in electrical communication with the plurality of pressure sensors and magnetic sources, the remote processing system programmed with one or more software routines executing on the remote processing system for: 1) activating the plurality of magnetic sources; 2) measuring the pressure sensed by each of the plurality of pressure sensors; and 3) determining the amount of metal in or within the construction structure of cylindrical shape. It is also preferred that the processing system be programmed with one or more software routines executing on the remote processing system for using the pressure measurements for constructing a volume image of the construction structure of cylindrical shape.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

The following detailed description of the exemplary embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1:
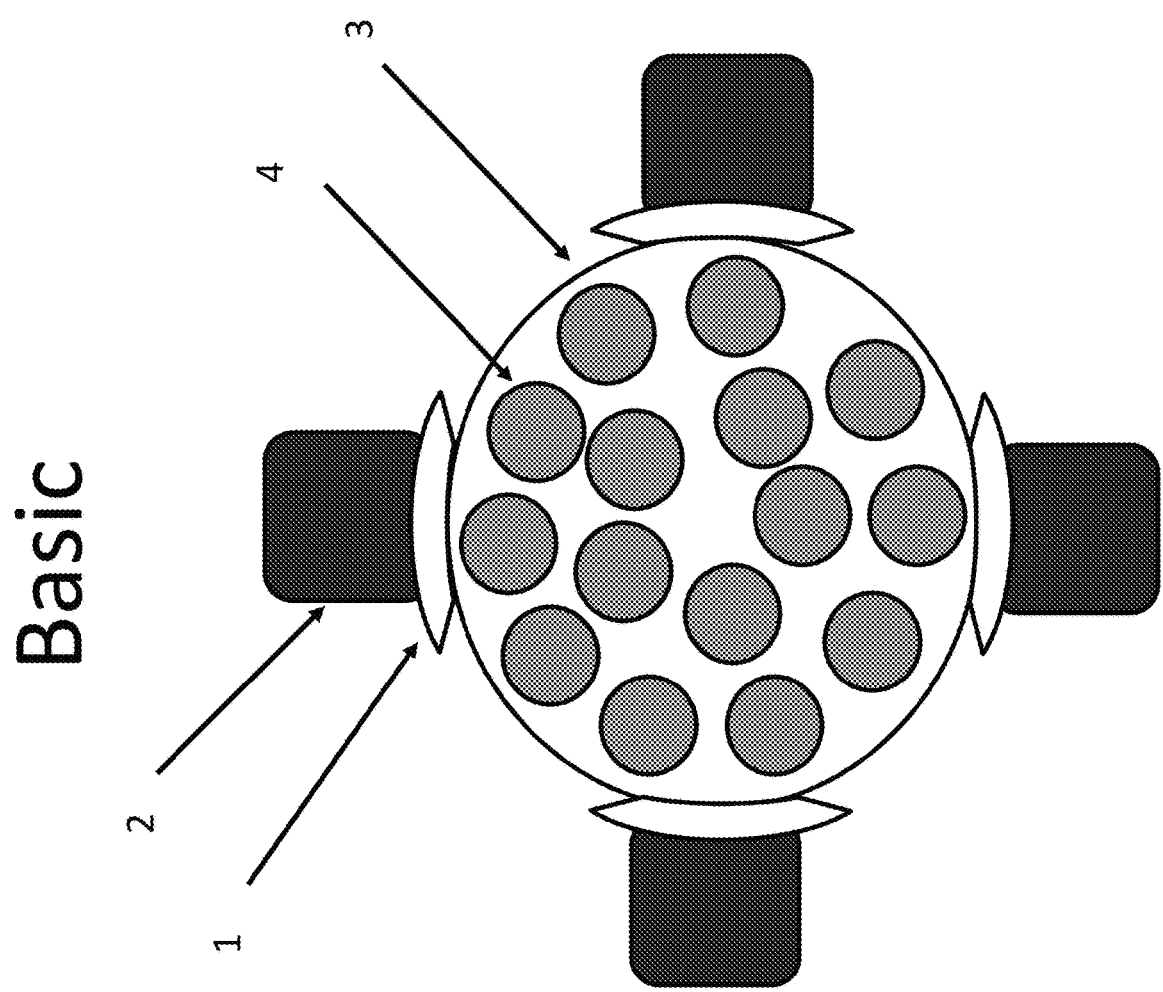
FIG. 1 illustrates one embodiment of Magnetic Pressure Sensor (MaPS) system including the magnetic source, pressure sensor, and a cross sectional view of a cylindrical structure with steel rods.

FIG. 1 illustrates one embodiment of a MaPS system composed of pressure sensors (1), magnetic sources (2), inspected structure (3) (e.g., tendon), and steel rods (4). (This embodiment shows four pairs of pressure sensors and magnetic sources). The magnetic sources (2) are attracted to the steel inside the structure being inspected and exert pressure on the pressure sensors (1). The pressure sensor is an electrical component that translates a pressure into an electric signal. In one example, pressure sensors are devices that change their electric resistance as a function of pressure, those are also called "strain gauges" and are used in many applications. This kind of pressure sensor is made up of conductive polymer material or spring element whose resistance changes when force or pressure is applied on the surface of the sensor. In another example, piezoelectric sensors comprised of two crystal disks with an electrode foil mounted in between can be used as the sensing device. When applying force, this results in an electrical charge that can be measured using a charge amplifier. The charge is proportional to the applied force.

In this embodiment, there are four pairs of pressure sensors and magnetic sources place around the inspected structure. Each of the outputs of the pressure sensors is a voltage signal proportional to the sensed pressure. In this invention, the pressure signal is used for measurement of the total steel mass inside the inspected structure. In the preferred embodiment, the signals from each magnetic source are analyzed separately. The outputs are individually analyzed and then combined in a frame format for estimation of steel mass in the cross-section and for image reconstruction. The collective pressure readings from all pressure sensors around the structure are used for image reconstruction of steel location within the tendon.

Figure 2:
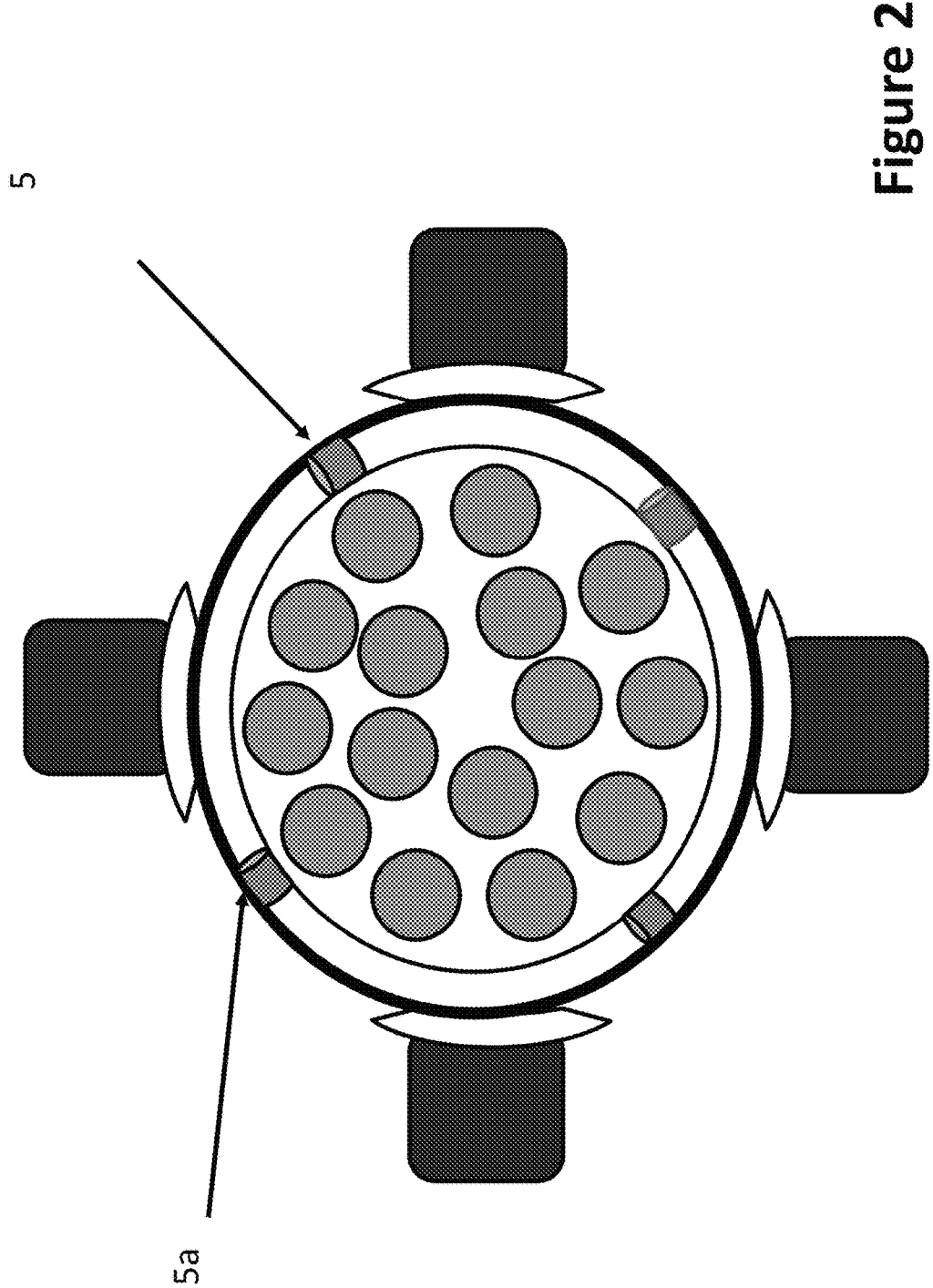
FIG. 2 illustrates one embodiment of the MaPS system in FIG. 1 with an intermediate surface between the system and the inspected structure.

FIG. 2 illustrates one embodiment of the MaPS system mounted on an intermediate surface (5) between the inspected object and the MaPS sensors. The intermediate surface here can skid or roll on the inspection surface. The intermediate structure holds the sensors in place and makes it independent from the inspected structure. It makes up the body of an instrument that uses these sensors to find metal. The material is preferably comprised of a thin plastic or polymer. In one embodiment, it can be equipped with rollers or wheels (5a) to move over pipes and tendons for fast inspection. The structure also provides a rigid surface to push against the magnet so the pressure is recorded by the pressure sensors.

Figure 3:
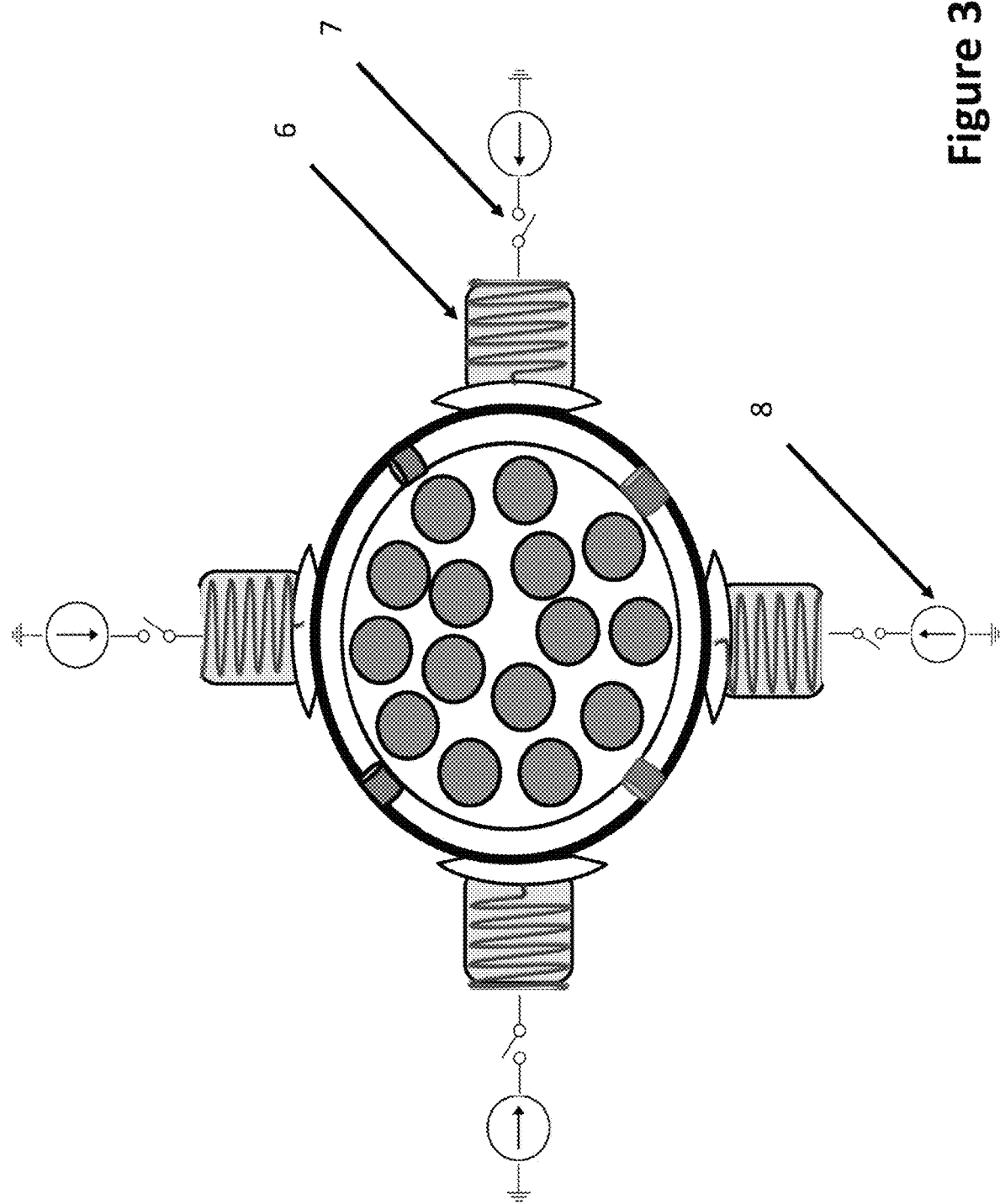
FIG. 3 illustrates a MaPS system where the magnetic source is constructed from windings around a ferromagnetic material with a current source.

FIG. 3 illustrates the embodiment of the magnetic source being electrically operated though windings around a magnetic material (6), a switch to turn on and off magnetization of the coils (7), and a current source (8). Upon closing of the switch, the current from the current source rushes though the windings and generates a magnetic field. The magnetic strength and pressure sensed by the pressure sensors in this case is a function of the number of winds, the current level, and the mass of steel. Pressure is measured by using a magnet (electric activated or permenant magnet) to generate a force by attracting to the steel inside the structure. The more steel in the structure, the higher the attraction and force. Measuring the voltage across the pressure sensor is directly correlated to the pressure it is subjected to. This voltage is then related to an amount of force on the sensor by a correlation plot [5 mV=2 lbs force, for example]. Voltage sensed from the MaPS system is used to measure and locate steel inside the inspected structure.

Figure 4:
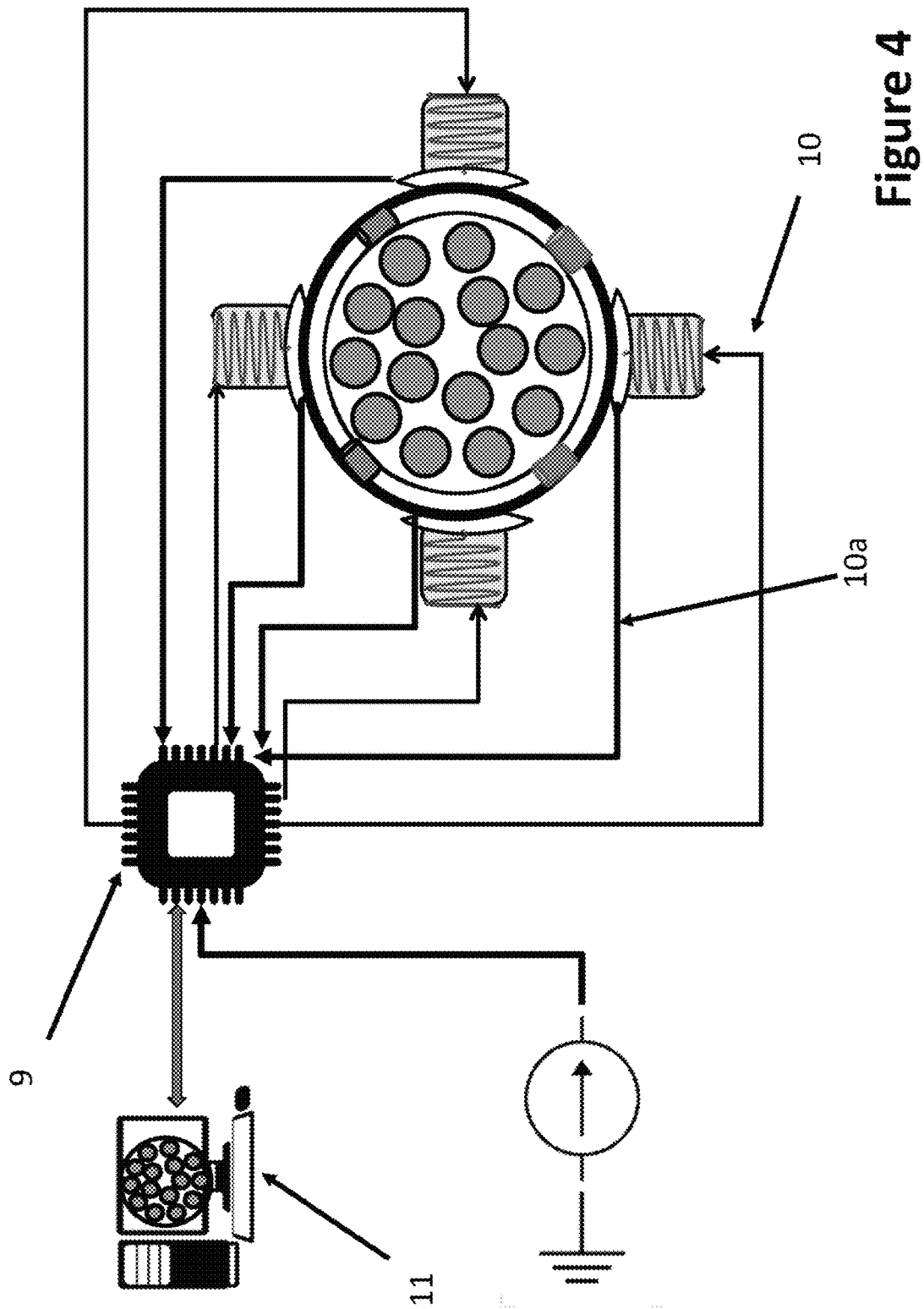
FIG. 4 illustrates one embodiment of the system where the magnetic sources are controlled electronically by a microcontroller or FPGA connected to a computer.

FIG. 4 illustrates one embodiment where a microcontroller or FPGA (9) is used to synchronize activation of the magnetic source through the current source and reporting back the voltage from each pressure sensor via control lines (10) and (10a) respectively. The data collected by the microcontroller/FPGA is communicated to a computer or smart device (11) for calculation of total steel mass and location.

Figure 5:
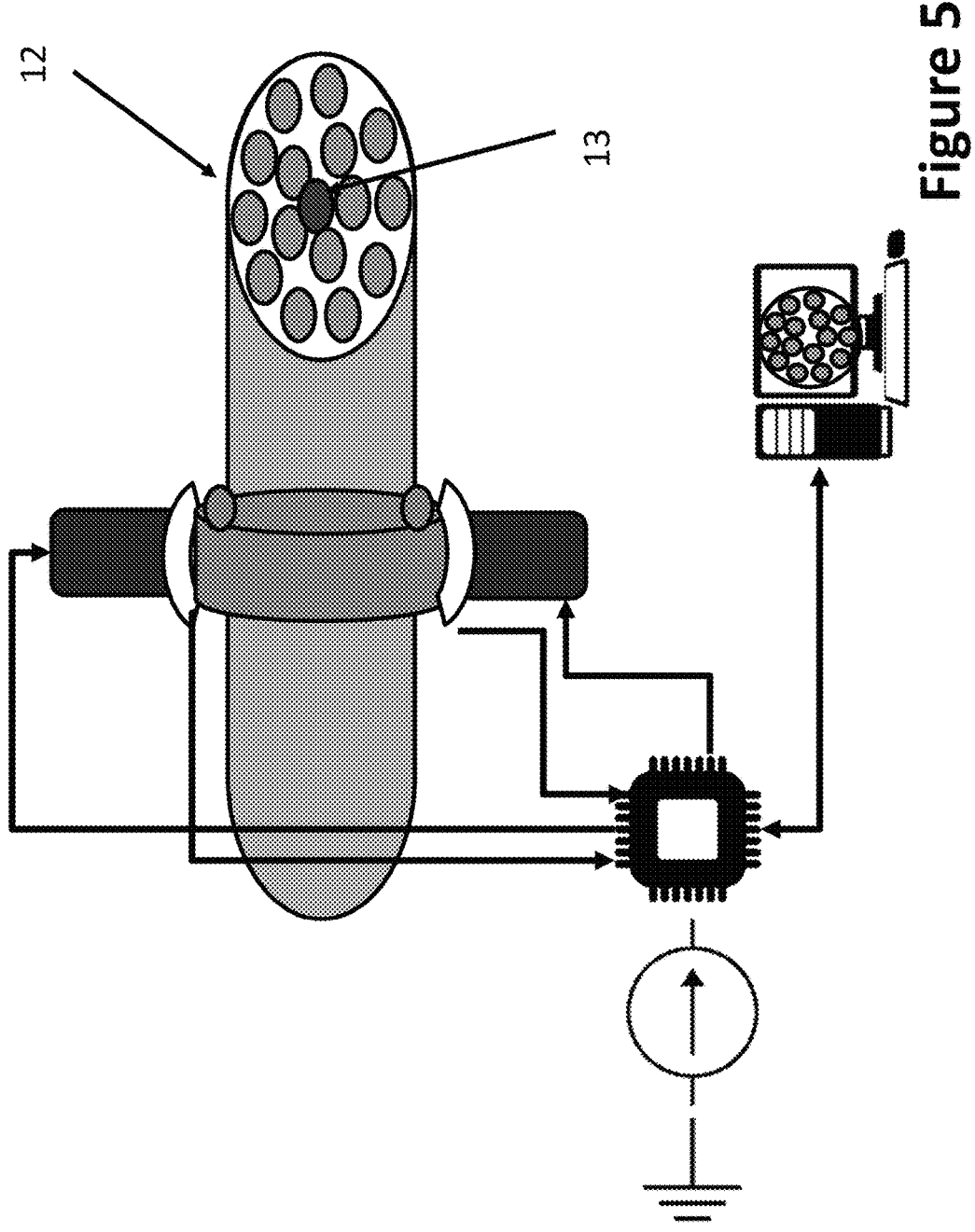
FIG. 5 illustrates the mounting of the MaPS system for rolling or skidding on the inspected tendon surface.

FIG. 5 illustrates the MaPS system sliding or rolling over a tendon (12). The sensors are housed on a rigid chassis with wheels, which roll along the surface of the inspected structure. The pressure sensor sends a voltage signal proportional to the attraction between the magnetic source and the equivalent center of steel attraction (13). The data sensed is used to determine if there is corrosion in the steel. The pressure system is calibrated on structures with having known and proper steel mass and steel location. Based on the readings from the pressure sensor, the force from all the sensors is related back to the calibration for estimation of steel mass inside the structure. This loss in metallic mass (based on lower pressure readings) is due to either corrosion or broken steel.

Figure 6:
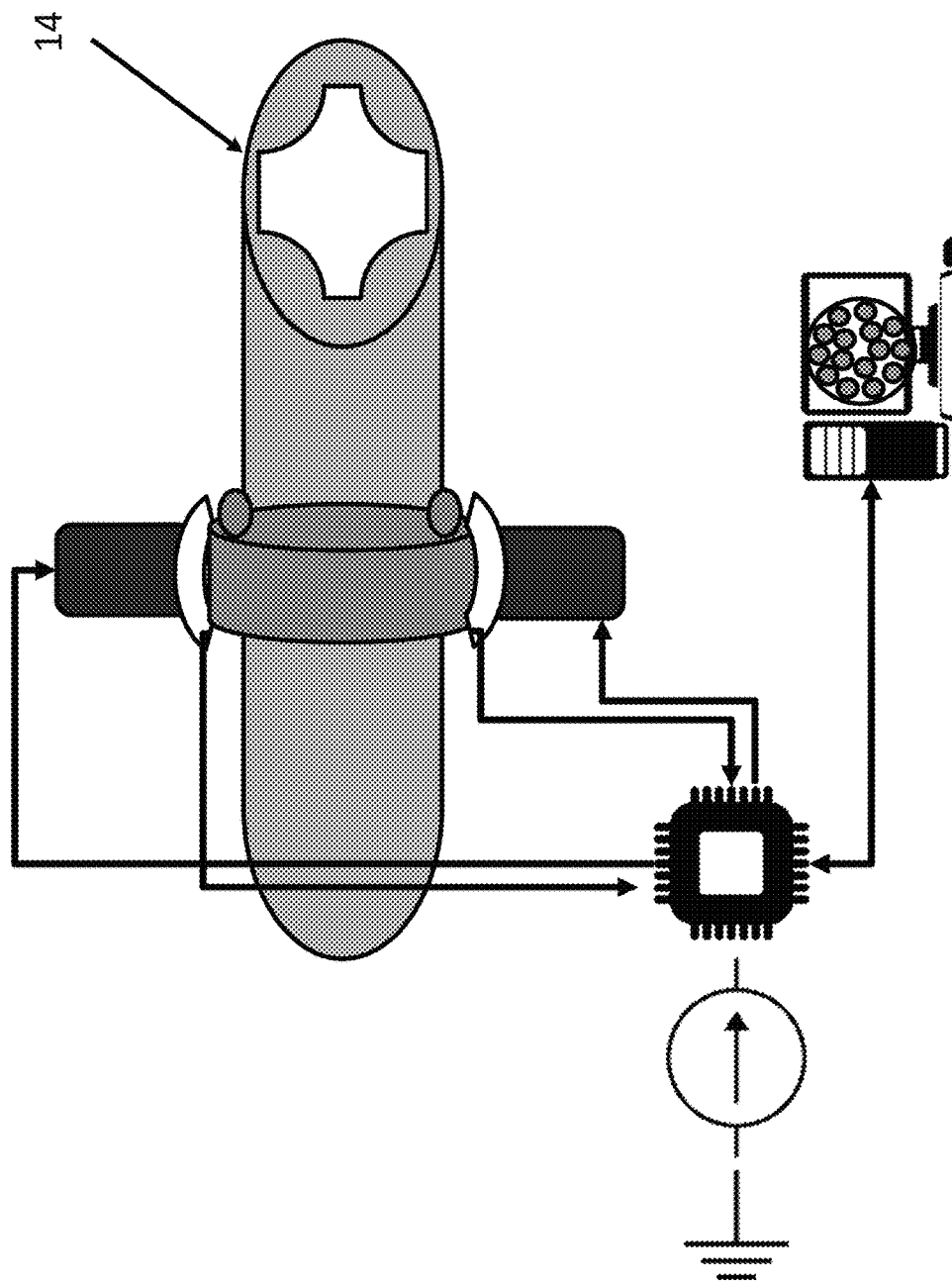
FIG. 6 illustrates the mounting of the MaPS system for rolling or skidding on the inspected steel or metal pipe surface. The pipe here has different thicknesses.

FIG. 6 illustrates the MaPS system sliding or rolling over a steel pipe (14) with different thicknesses across its cross-section. The pressure sensor sends a voltage signal proportional to the attraction between the magnetic source and the thickness of steel in the pipe. A thicker steel wall will produce a larger amount of force on the pressure sensors immediately above that part of the wall. The difference between pressure sensor readings can be used to determine the thickness of steel at each sensor region. The system will be calibrated to relate a certain amount of force to a certain thickness of the steel wall.

Figure 7:
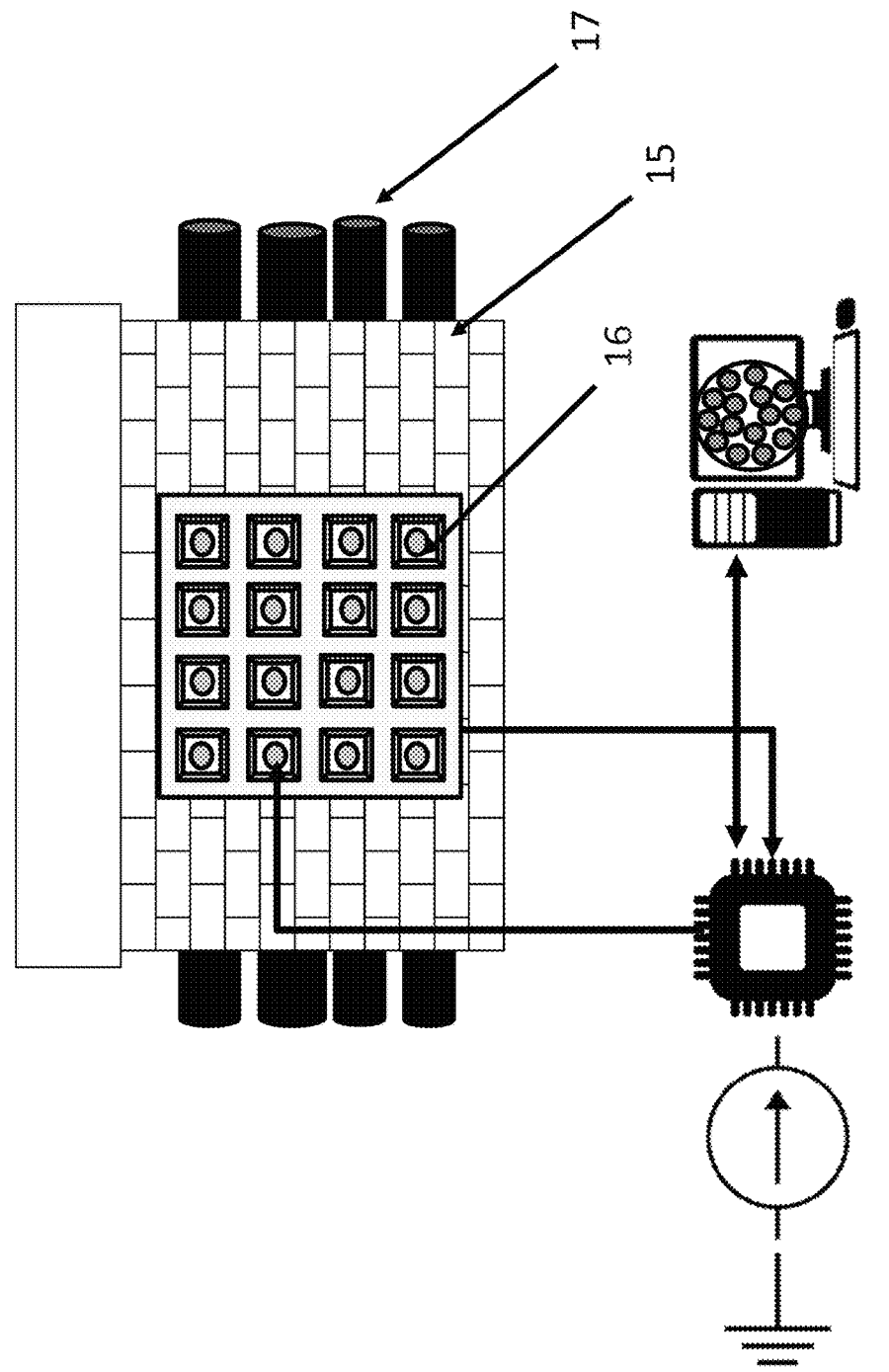
FIG. 7 illustrates one embodiment of the MaPS system mounted on a flat surface.

FIG. 7 illustrates the MaPS system sliding or rolling over a flat surface or wall (15). The MaPS system in this case is arranged horizontally (16) (instead of around the cylindrically shaped pipe or tendon) and the pressure sensors signal is proportional to the steel mass (17) inside or behind the flat surface. An FPGA or controller reads the data from each magnetic sensor and sends it to computer processing system for further processing. Each square shown in FIG. 7 represents a magnetic source and pressure sensor pair.

Figure 8:
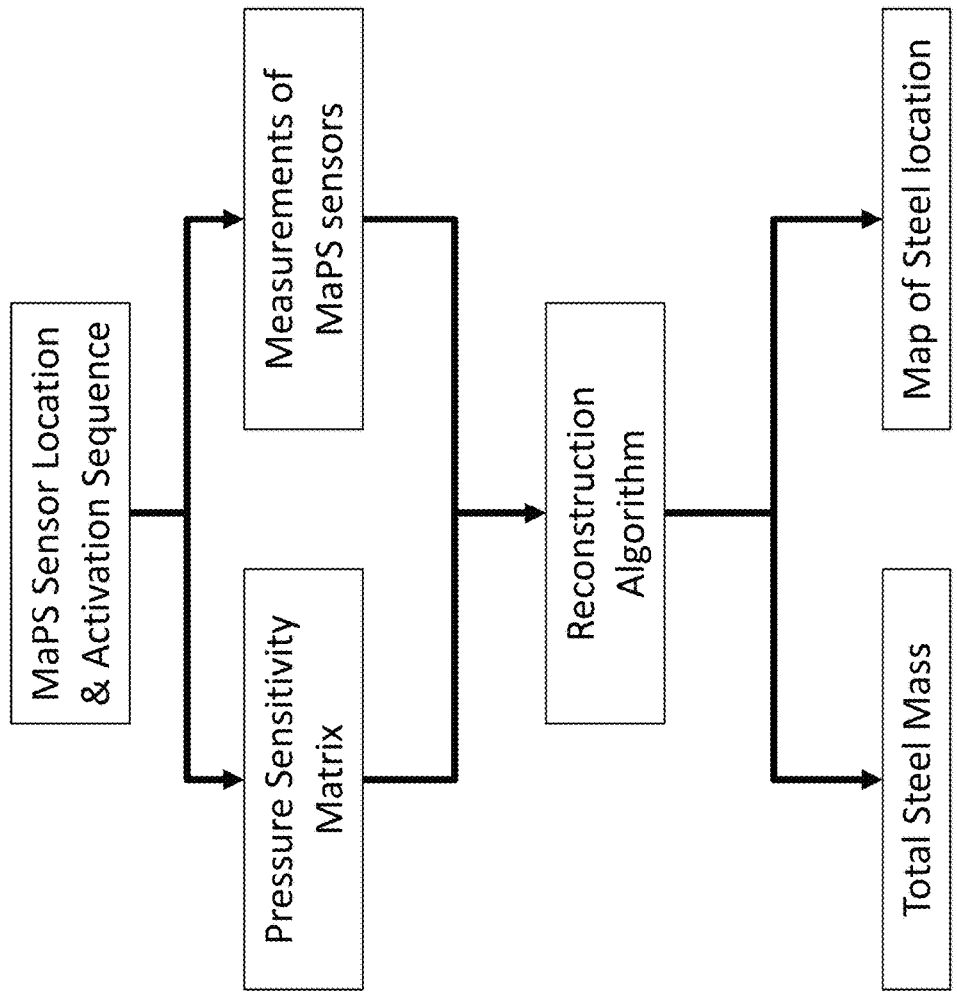
FIG. 8 illustrates one embodiment of the MaPS process.

FIG. 8 illustrates the flow process of positioning and activating the MaPS sensors toward measurement of total mass loss and location of steel. The algorithm is built by relating a certain pressure reading to different amounts and locations of steel within the inspected region. Enough data is gathered to form relations between magnetic pressure readings and steel amount and location. In device operation, pressure readings will be inputs into the algorithm which translates the readings into steel quantity and location based on such calibration data. The recorded calibration and sensitivity data is recorded in a sensitivity matrix that relates the system response to steel mass and location. The reconstruction algorithm is similar to the one used in ECVT and AECVT in that it uses a sensitivity matrix to perform reconstruction.

While certain embodiments of the present invention are described in detail above, the scope of the invention is not to be considered limited by such disclosure, and modifications are possible without departing from the spirit of the invention as evidenced by the following claims.

What is claimed is:

1. A system for determining an amount of metal in a construction member of cylindrical shape, the system comprising:
a plurality of pressure sensors adapted to be placed around an exterior surface of the construction member of cylindrical shape;
a plurality of magnetic sources, wherein each of the plurality of magnetic sources is paired with one of the plurality of pressure sensors, and wherein each pair of pressure sensor and magnetic source is arranged such that the pressure sensor is positioned between the respective magnetic source and the construction member of cylindrical shape during the system operation, and wherein each of the plurality of pressure sensors are adapted to sense pressure experienced at the pressure sensor resulting from attracting magnetic forces exerted between each of the plurality of magnetic sources and the metal in or within the construction member of cylindrical shape;
a remote processing system in electronic communication with the plurality of pressure sensors and the plurality of magnetic sources, the remote processing system comprising one or more executable software routines, which when executed, configure the remote processing system to: 1) activate the plurality of magnetic sources; 2) measure the pressure sensed by each of the plurality of pressure sensors; and 3) determine the amount of metal in or within the construction member of cylindrical shape; and
an intermediate structure placed between the construction member of cylindrical shape and the plurality of pressure sensors, the intermediate structure adapted to skid or roll on an outside surface of the construction member of cylindrical shape.

2. The system of claim 1, wherein the remote processing system comprises one or more additional executable software routines, which when executed, configure the remote processing system to: 1) construct a volume image of the construction member of cylindrical shape based upon the pressure measurements sensed by each of the plurality of pressure sensors.

3. The system of claim 1, further comprising:
a plurality of switches, each of the switches operationally connected to one of the plurality of magnetic sensors.

4. The system of claim 1, wherein the intermediate structure is comprised of a thin plastic or polymer and a set of wheels.

5. The system of claim 1, further comprising:
a plurality of current sources each operationally connected to one of the plurality of magnetic sources.

6. The system of claim 5, wherein each of the magnetic sources is comprised of windings configured to generate a magnetic field when activated by one of the plurality of current sources.

7. The system of claim 1, wherein each of the plurality of pressure sensors is adapted to generate a voltage signal proportional to the attractive magnetic forces between one of the magnetic sources and the metal in or within the construction member of cylindrical shape.

8. The system of claim 1, wherein the remote processing system comprises one or more additional executable software routines, which when executed, configure the remote processing system to calibrate the system based on a construction member having a known metal mass and location and determine metal mass in or within the construction member of cylindrical shape based upon calibration information.

9. The system of claim 1, wherein the pressure sensors are strain gauges.

10. The system of claim 1, wherein the remote processing system comprises one or more additional software routines, which when executed, configure the remote processing system to determine the thickness of metal of the construction member of cylindrical shape.

11. A system for determining an amount of metal in a construction member of cylindrical shape, the system comprising:
a plurality of pressure sensors adapted to be placed around an exterior surface of the construction member of cylindrical shape;
a plurality of magnetic sources, wherein each of the plurality of magnetic sources is paired with one of the plurality of pressure sensors, and wherein each pair of pressure sensor and magnetic source is arranged such that the pressure sensor is positioned between the respective magnetic source and the construction member of cylindrical shape during the system operation, and wherein each of the plurality of pressure sensors are adapted to sense pressure created by attracting magnetic forces exerted between each of the plurality of magnetic sources and the metal in or within the construction member of cylindrical shape which result in compressive forces experienced at a sandwiched pressure sensor;

a remote processing system in electronic communication with the plurality of pressure sensors and plurality of magnetic sources, the remote processing system comprising one or more executable software routines, which when executed, configure the remote processing system to: 1) activate the plurality of magnetic sources; 2) measure the pressure sensed by each of the plurality of pressure sensors; 3) determine the amount of metal in or within the construction member of cylindrical shape; and 4) generate a volume image of the metal in or within the construction member of cylindrical shape; and an intermediate structure placed between the construction member of cylindrical shape and the plurality of pressure sensors, the intermediate structure comprising a polymer housing and a set of wheels, wherein the intermediate structure is adapted to roll along an outside surface of the construction structure of cylindrical shape.

12. The system of claim 11, further comprising:
a plurality of switches, each of the switches operationally connected to one of the plurality of magnetic sensors; and
a plurality of current sources each operationally connected to one of the plurality of magnetic sources, wherein each of the magnetic sources is comprised of windings for generating a magnetic field when activated by one of the plurality of current sources, and wherein each of the plurality of pressure sensors is adapted to generate a voltage signal proportional to the attractive magnetic forces between one of the magnetic sources and the metal in or within the construction member of cylindrical shape.

13. The system of claim 11, wherein the remote processing system comprises one or more additional executable software routines, which when executed, configure the remote processing system to calibrate the system based on a construction member having a known metal mass and location.

14. A system for determining an amount of metal in a construction structure having an exterior flat surface, the system comprising:
a plurality of pressure sensors adapted to be placed on the exterior flat surface of the construction structure in a grid;
a plurality of magnetic sources, wherein each of the plurality of magnetic sources is paired with one of the plurality of pressure sensors, and wherein each pair of pressure sensor and magnetic source is arranged such that the pressure sensor is positioned between the respective magnetic source and the construction structure during the system operation, and wherein each of the plurality of pressure sensors are adapted to sense pressure experienced at the pressure sensor resulting from attracting magnetic forces exerted between each of the plurality of magnetic sources and the metal in or within the construction structure;

a remote processing system in electronic communication with the plurality of pressure sensors and the plurality of magnetic sources, the remote processing system comprising one or more executable software routines, which when executed, configure the remote processing system to: 1) activate the plurality of magnetic sources; 2) measure the pressure sensed by each of the plurality of pressure sensors; and 3) determine the thickness of metal in or within the construction structure; and an intermediate structure placed between the construction structure and the plurality of pressure sensors, the intermediate structure adapted to skid or roll on the outside surface of the construction structure.

15. The system of claim 14, wherein the remote processing system comprises one or more additional executable software routines, which when executed, configure the remote processing system to construct a volume image of the construction structure based upon the pressure measurements.

16. The system of claim 14, further comprising:
a plurality of switches, each of the switches operationally connected to one of the plurality of magnetic sensors; and
a plurality of current sources each operationally connected to one of the plurality of magnetic sources, wherein each of the magnetic sources is comprised of windings for generating a magnetic field when activated by one of the plurality of current sources, and wherein each of the plurality of pressure sensors is adapted to generate a voltage signal proportional to the attractive magnetic forces between one of the magnetic sources and the metal in or within the construction structure.

17. The system of claim 14, wherein the intermediate structure is comprised of a thin plastic or polymer and a set of wheels.

* * * * *